US010507136B2

(12) United States Patent
Lemonis et al.

(10) Patent No.: US 10,507,136 B2
(45) Date of Patent: Dec. 17, 2019

(54) APPARATUS FOR LASER PROCESSING AN EYE

(71) Applicant: Novartis AG, Basel (CH)

(72) Inventors: Sissimos Lemonis, Erlangen (DE); Peter Riedel, Erlangen (DE); Mario Abraham, Burgthann (DE)

(73) Assignee: Novartis AG (CH)

( * ) Notice: Subject to any disclaimer, the term of this patent is extended or adjusted under 35 U.S.C. 154(b) by 0 days.

(21) Appl. No.: 15/514,460

(22) PCT Filed: Nov. 20, 2014

(86) PCT No.: PCT/EP2014/075076
§ 371 (c)(1),
(2) Date: Mar. 24, 2017

(87) PCT Pub. No.: WO2016/078707
PCT Pub. Date: May 26, 2016

(65) Prior Publication Data
US 2017/0281406 A1 Oct. 5, 2017

(51) Int. Cl.
*A61F 9/00* (2006.01)
*A61B 3/00* (2006.01)
(Continued)

(52) U.S. Cl.
CPC .............. *A61F 9/008* (2013.01); *A61B 3/113* (2013.01); *A61F 2009/00846* (2013.01)

(58) Field of Classification Search
CPC ........ A61F 9/007; A61F 9/008; A61F 9/0008; A61F 2009/00844; A61F 2009/00846;
(Continued)

(56) References Cited

U.S. PATENT DOCUMENTS 8,764,187 B2 * 7/2014 Padrick ............... A61F 2/16
351/159.73
9,216,110 B2 * 12/2015 Vogler ............... A61F 9/008
(Continued)

FOREIGN PATENT DOCUMENTS

JP 2005-528600 A 9/2005
WO 2003/102498 A1 12/2003
(Continued)

OTHER PUBLICATIONS

Using Matlab Graphics, 2005, Version 7.*
(Continued)

*Primary Examiner* — Michael W Kahelin
*Assistant Examiner* — Sana Sahand
(74) *Attorney, Agent, or Firm* — Keiko Ichiye, Esq.

(57) ABSTRACT

An ophthalmic laser processing apparatus comprises: a laser device that outputs a pulsed laser beam towards an eye; an image capturing device that captures an image of the eye and provides image data; and a control device that detects eye movement based on the image data and controls the beam focus based on a predetermined eye processing pattern and the eye movement. The apparatus further comprises a visualization device controlled by the control device to output a visualization of a graphical illustration. The graphical illustration represents at least one of (a) a value of an eye parameter determined on the basis of the image data; (b) a frequency distribution of a value of an eye parameter determined on the basis of the image data; and (c) a range of values of a pupil diameter determined on the basis of the image data.

19 Claims, 4 Drawing Sheets

(51) Int. Cl.
*A61F 9/008* (2006.01)
*A61B 3/113* (2006.01)

(58) Field of Classification Search
CPC ......... A61B 3/12; A61B 3/113; A61B 5/7275; A61B 9/008
USPC ................................. 351/200, 206, 209, 210
See application file for complete search history.

(56) References Cited

U.S. PATENT DOCUMENTS

| | | | | |
|---|---|---|---|---|
| 9,498,117 | B2* | 11/2016 | Dai | A61B 3/028 |
| 9,504,376 | B2* | 11/2016 | Neal | A61B 3/0025 |
| 9,596,983 | B2* | 3/2017 | Chernyak | A61B 3/1015 |
| 9,782,064 | B1* | 10/2017 | Linder | A61B 3/0025 |
| 2003/0223037 | A1* | 12/2003 | Chernyak | A61B 3/1015 351/209 |
| 2004/0012760 | A1* | 1/2004 | Mihashi | A61B 3/1015 351/205 |
| 2005/0024586 | A1 | 2/2005 | Teiwes et al. | |
| 2009/0247997 | A1* | 10/2009 | Watanabe | A61F 9/008 606/4 |
| 2014/0313488 | A1* | 10/2014 | Kiderman | A61B 3/145 351/246 |

FOREIGN PATENT DOCUMENTS

| | | | | |
|---|---|---|---|---|
| WO | WO-2012154278 A1 * | 11/2012 | ........... | A61B 3/0058 |
| WO | 2013156046 A1 | 10/2013 | | |

OTHER PUBLICATIONS

Graphing Using Matlab: The Lanaguage of Technical Computing, Feb. 11, 2005, The MathWorks, Version 7.*
Graphing Using Matlab: The Language of Technical Computing, Feb. 11, 2005, The MathWorks, Version 7 (Year: 2005).*
Wavelight GMBH; Wavelight EX500 Excimer Laser; Alcon a Novartis Company; 2013 Novartis; pp. 1-37.

* cited by examiner

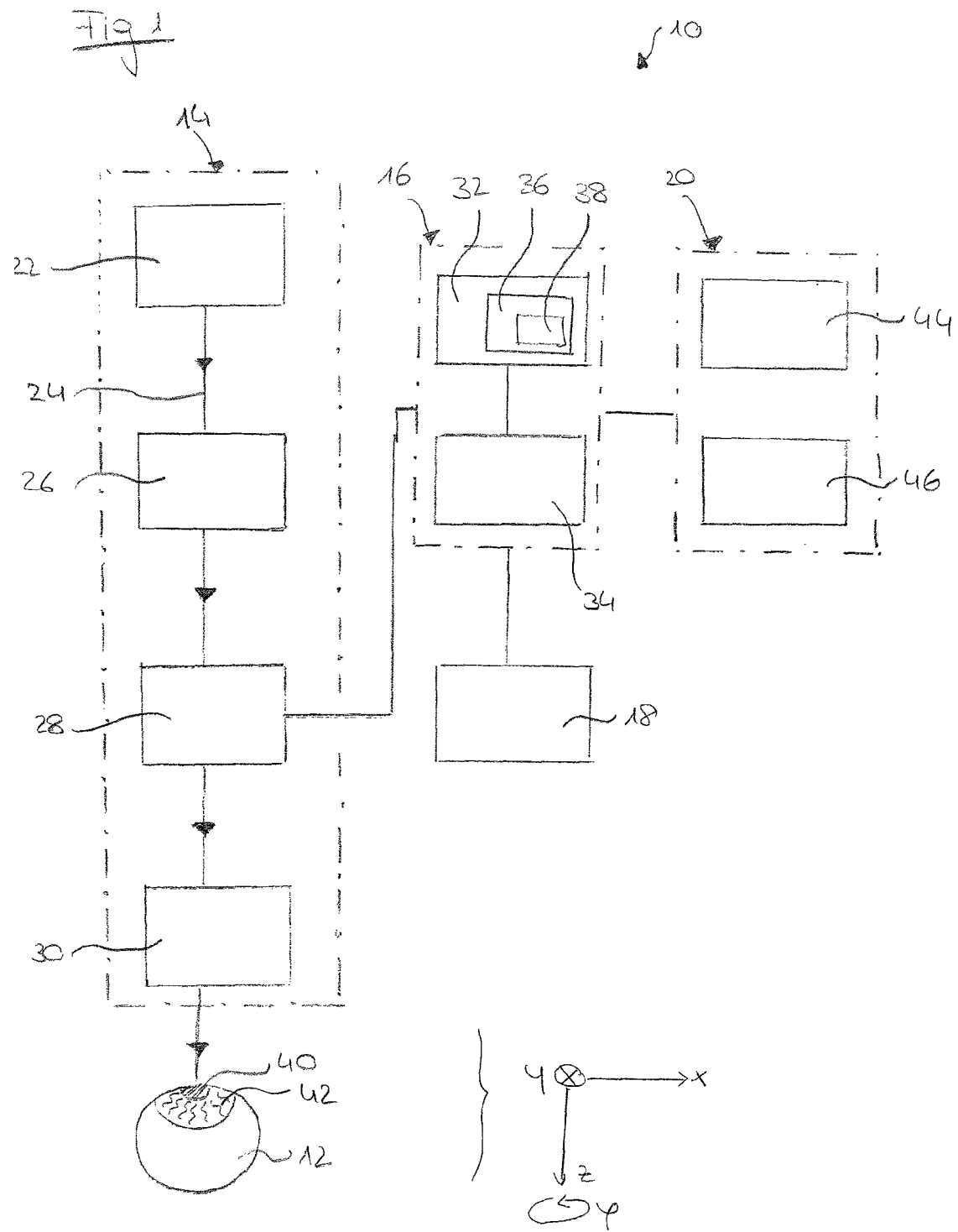

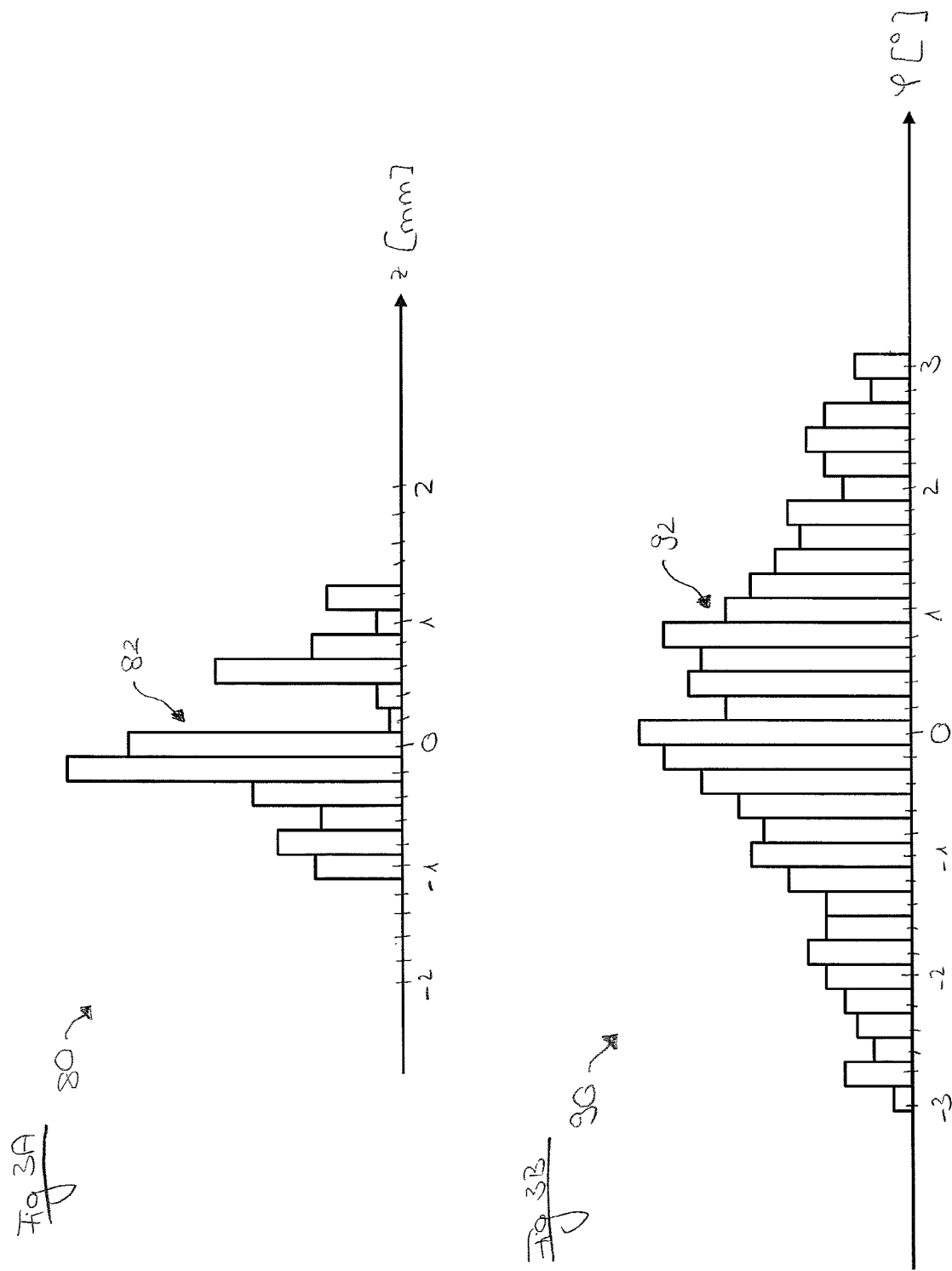

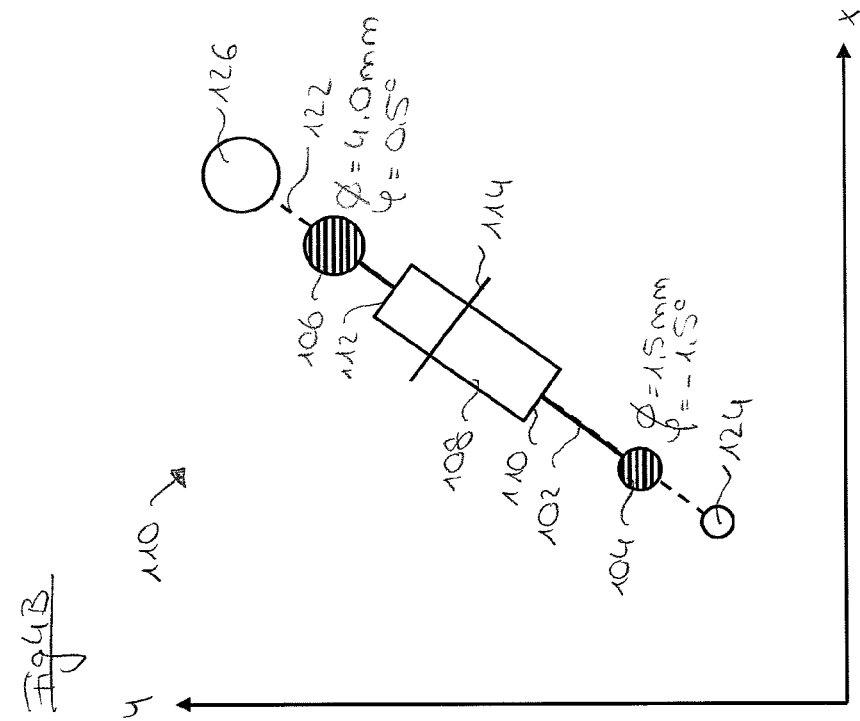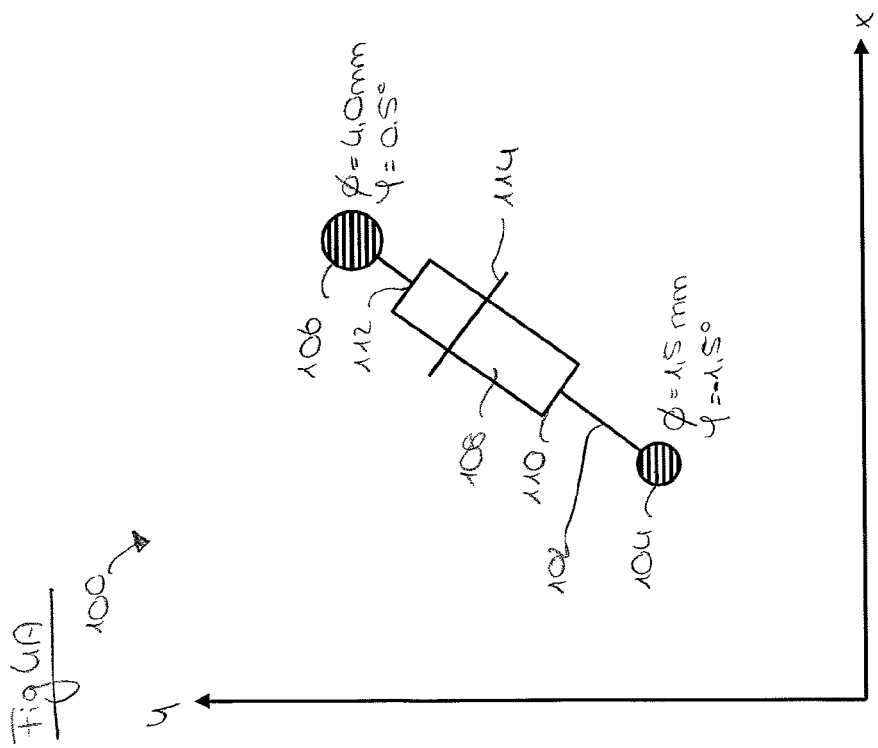

APPARATUS FOR LASER PROCESSING AN EYE

CROSS REFERENCE TO RELATED APPLICATIONS

This application is a section 371 national stage phase of International Application No. PCT/EP2014/075076, filed 20 Nov. 2014, titled "AN APPARATUS FOR LASER PROCESSING AN EYE," which is hereby incorporated by reference in its entirety.

TECHNICAL FIELD

The present disclosure generally relates to an apparatus for laser processing an eye, and more particularly relates to a laser processing apparatus capable of visualizing one or more eye parameters as they change during the course of a laser treatment procedure.

BACKGROUND

Laser radiation may be used for processing a human eye. In a conventional laser treatment procedure, focused laser radiation is utilized to remove tissue from an exposed surface of the eye or create an incision in tissue of the eye. The removal process is oftentimes referred to as ablation in the conventional art. Whatever the physical effect (i.e. ablation or creation of an incision), a general requirement is that a focus of the radiation be steered in a precisely controlled manner in time and space so that every radiation pulse hits the eye at a desired target location.

While for the creation of an incision a patient's eye is conventionally held in a fixed position with respect to a laser apparatus delivering the radiation (through contact with a contact element of the apparatus), an ablating procedure is conventionally performed without the eye being positionally fixed. In the course of an ablating procedure, changes in eye position with respect to the laser apparatus due to a human eye's natural (and inevitable) movement or due to movement of the patient's head may thus occur. The changes in eye position may include a displacement in one or more translational directions and, alternatively or additionally, a displacement about one or more rotational axes. An eye-tracker may be used to detect eye movement and keep track of the eye's position. The eye-tracker includes one or more cameras to acquire images of the eye. Through image processing of the acquired images, a current position of the eye with respect to a coordinate system of the laser apparatus may be determined, and the determined current position may be used as a reference for aligning (centering) a shot pattern for the laser radiation. Conventionally, a position of a center of the pupil is determined as a reference position for alignment of the shot pattern. The position of the pupil center can be determined based on a detection of the margin of the pupil (i.e. iris) in the images captured by the eye-tracker. Further, it is conventionally known that the pupil center position as measured with respect to a coordinate system of the laser apparatus may shift as a result of variations of the pupil diameter. Thus, changes in ambient brightness may cause a shift of the pupil center even in the absence of eye movement.

Where an eye-tracker includes rotational tracking functionality, rotational movement of the eye can be tracked and taken into account in controlling the position of the radiation focus. For example, dynamic cyclotorsion of the eye may occur during an ablating procedure. Cyclotorsion generally refers to a rotation about an optical axis of the eye. Accordingly, whenever cyclotorsion occurs, the shot pattern should be adjusted by applying a rotational offset to account for the cyclotorsion. In addition, the optical axis may traverse the pupil at a position offset from the pupil center. A cyclotorsional movement of the eye may therefore bring with it a shift of the pupil center, requiring a translatory offset of the shot pattern to account for the pupil center shift.

The laser treatment can be a stressful experience for the patient. Nervousness of the patient typically reflects in an increased amount of natural eye movement of the patient and may also reflect in changes of the pupil diameter. A feeling of uneasiness or anxiety may also be reason for abrupt and jerking moves of the patient's eye or patient's head. If a patient is overly nervous, it may be advisable to interrupt an ongoing operation and continue at a later time after the patient has calmed down.

BRIEF SUMMARY

Embodiments of the present invention provide a tool allowing visualization of tracking information acquired by an eye-tracker in the course of an ophthalmic laser procedure.

According to an embodiment, an ophthalmic laser processing apparatus is provided. The apparatus comprises: a laser device configured to output a pulsed laser beam towards an eye, the laser beam having a beam focus; an image capturing device positioned to capture an image of the eye and configured to provide image data; and a control device configured to detect eye movement based on the image data and to control the beam focus temporally and spatially based on a predetermined eye processing pattern and the detected eye movement. The apparatus further comprises a visualization device controlled by the control device to output a visualization of a graphical illustration. The graphical illustration represents at least one of: (a) a value of an eye parameter determined on the basis of the image data in relation to each of a plurality of different time points or time intervals; (b) a frequency distribution of a value of an eye parameter determined on the basis of the image data in relation to each of a plurality of different time points or time intervals; and (c) a range of values of a pupil diameter determined on the basis of the image data in relation to each of a plurality of different time points or time intervals.

The laser device may comprise a source of pulsed laser radiation. The laser device may further comprise a focusing device disposed behind the laser source in beam propagation direction. The focusing device may be a focusing objective or a different optical device to focus the laser beam emitted by the laser source. The image capturing device and at least parts of the control device may be comprised by a multi-dimensional eye-tracker. The eye-tracker, for example, may include a camera and an image processing unit for processing the images acquired by the camera.

The control device may be configured to determine (on the basis of the provided image data) at least one attribute of the value of the eye parameter, the frequency distribution of the value of the eye parameter and the range of values of the pupil diameter. It may be provided that the graphical illustration may represent the determined attribute in relation to each of a plurality of pulses of the laser beam. Alternatively, it may be provided that the graphical illustration thereof may represent the determined attribute in relation to each of a plurality of pulse sequences (e.g., in relation to the first pulse of the pulse sequence or averaged over each of the pulses within the pulse sequence). The plurality of pulses may be, or may include, temporally successive pulses.

The eye parameter may be a position of a pupil center. In this case, the pupil center position may be a position with respect to an x-y coordinate plane oriented orthogonally to an output direction of the laser beam. The output direction may correspond to the beam propagation direction behind the focusing device. It may be provided that the graphical illustration represents the position of the pupil center as an x-y offset with respect to an x-y reference position of the pupil center, wherein the x-y reference position is defined as an x-value of 0 and a y-value of 0 in the x-y coordinate plane. The graphical illustration, in this case, may represent x-y offset values within a range of −3 mm to +3 mm in steps of 0.2 mm. Alternatively, the range and/or the step size can take any suitable values (e.g., a range of −5 mm to 5 mm in steps of 0.5 mm). The x-y offset values may, for example, be caused by movements of the patient's head and/or movements of the eye within an eye socket with respect to the apparatus. The x-y reference position of the pupil center of the eye may be determined before the laser processing starts or may correspond to the first x-y position determined at the plurality of different time points or time intervals.

The eye parameter may be further an eye position with respect to a z-axis oriented in the output direction of the laser beam. Different eye positions along the z-axis may occur, for example, due to head movements of the patient in relation to the apparatus. As an alternative or in addition to this, the eye parameter may be indicative of a rotational position of the eye. In this case, the eye parameter may indicate an amount of cyclorotation (cyclotorsional movements) of the eye. The amount of cyclorotation may be denoted as eye position with respect to a φ-axis. It may be provided that the eye position with respect to the z-axis and/or to the φ-axis is represented by the graphical illustration as an offset value with respect to a reference value.

For visualization purposes, the graphical illustration may represent the value of the eye parameter by a graphical object having identical appearance for each time point or time interval. As an alternative, different time intervals may be represented by different graphical objects or by the same graphical object having different appearances (e.g., different colors). The graphical object may, for example, be a dot, a cross, a line, an oval, a polygon, an asterisk or any other geometrical object.

The control device may be configured to determine the value of the eye parameter in relation to each of a plurality of pulses of the laser beam and to determine the frequency distribution on the basis of the determined parameter values. The graphical illustration may represent different frequencies of the value of the eye parameter through at least one of different degrees of transparency and different colors of the graphical object. In this case, the eye parameter may, for example, be the position of the pupil center with respect to the x-y coordinate plane. As an alternative to this, the graphical illustration may represent the frequency distribution in the form of a histogram including bars having a frequency-dependent size. In this case, the frequency distribution may be determined on the basis of, for example, the eye position with respect to the z-axis and/or to the φ-axis.

For the purpose of visualizing the range of values of the pupil diameter, the control device may be configured to determine a pupil diameter value on the basis of the image data in relation to each of a plurality of pulses of the laser beam. As the eye typically performs cyclorotational movements in accordance with the change of the pupil diameter, the control device may be further configured to determine the respective eye positions with respect to the φ-axis and/or the position of a pupil center with respect to the x-y coordinate plane.

It may be provided that the control device is configured to determine upper and lower limit values for the range of values based on the determined pupil diameter values, wherein the graphical illustration represents the determined upper and lower limit values. In this case, the control device may be further configured to determine an average value or a median value of the pupil diameter based on the determined pupil diameter values, wherein the graphical illustration further represents the determined average or median value. The graphical illustration may represent the upper and lower limit values and the determined average or median value by respective graphical objects, wherein a graphical object for the average or median value is located between graphical objects for the upper and lower limit values. A proportion of distances of the graphical object for the average or median value from the graphical objects for the upper and lower limit values may correspond to a proportion of differences between the average or median value and the upper and lower limit values. Alternatively or additionally, different values (e.g., upper and lower limits of a standard deviation of the pupil diameter around the average value) for the range of values may be determined by the control device and represented by the graphical illustration.

The graphical illustration may represent at least one reference range of values of the pupil diameter, wherein a lower limit value of the reference range of values is indicative of a value of the pupil diameter at a first reference brightness and an upper limit value of the reference range of values is indicative of a value of the pupil diameter at a second reference brightness. The reference range of values in this case may extend over a range of pupil diameters as typically occurring during the course of laser processing the eye. It may be provided that the reference range of values is based on pupil diameters determined in the course of a reference measurement of pupil diameters of the patient (e.g., previously to the laser processing). Alternatively or additionally, it may be provided that the reference range of values is based on averaged empirical data determined in the course of reference measurements of pupil diameters of different patients. The at least one reference range of values may be stored in the control device or in memory accessible to the control device.

The graphical illustration may represent the range of values and/or the reference range of values in a two-dimensional visualization area spanned by an x-y coordinate plane oriented orthogonally to the output direction of the laser beam. In this case, the graphical illustration may include at least one graphical object representing a value of the pupil diameter and having an x-y position in the visualization area corresponding to an x-y position of the pupil center in the x-y coordinate plane at the value of the pupil diameter. For the purpose of visualizing the reference range of values, it may be provided that the graphical illustration includes a rectilinear line. For the purpose of visualizing the range of values, it may be provided that the graphical illustration includes one or more bars extending transversely to the rectilinear line. The bars may be part of a box superimposed over the rectilinear line. In an alternative embodiment, the box may be show next to the rectilinear line.

In order to enable a follow-up of a laser procedure, the control device may be configured to cause the visualization device to output the graphical illustration during a phase of beam emission and to update the graphical illustration as the phase of beam emission proceeds. This allows an operator to observe the visualized graphical illustration as a surgical procedure proceeds and, for example, to intervene by halting the procedure if he finds that the patient is too nervous and should be calmed down. In certain embodiments, an update of the visualized graphical illustration may be instructed by the control device at regular intervals counted as a number of pulses of the emitted laser beam. For example, an update may be instructed every 100 or 50 or 20 or 10 pulses or even after every single pulse of the emitted beam. In other embodiments, the control device may be configured to cause the visualization device to output the graphical illustration only after completion of a phase of beam emission. The visualization device may include at least one of a monitor and a printer.

BRIEF DESCRIPTION OF THE DRAWINGS

Additional features, advantages or elements of the present invention may be gathered from the following description of the accompanying drawings, in which:

FIG. 1 schematically shows a block diagram of an ophthalmic laser processing apparatus according to an exemplary embodiment;

FIGS. 3A and 3B schematically show exemplary graphical illustrations including frequency histograms for a z-position and a cyclorotation, respectively, of an eye, according to embodiments; and FIGS. 4A and 4B schematically show exemplary graphical illustrations to visualize a pupil center shift of an eye, according to embodiments.

DESCRIPTION OF EXAMPLE EMBODIMENTS

Figure 2B:
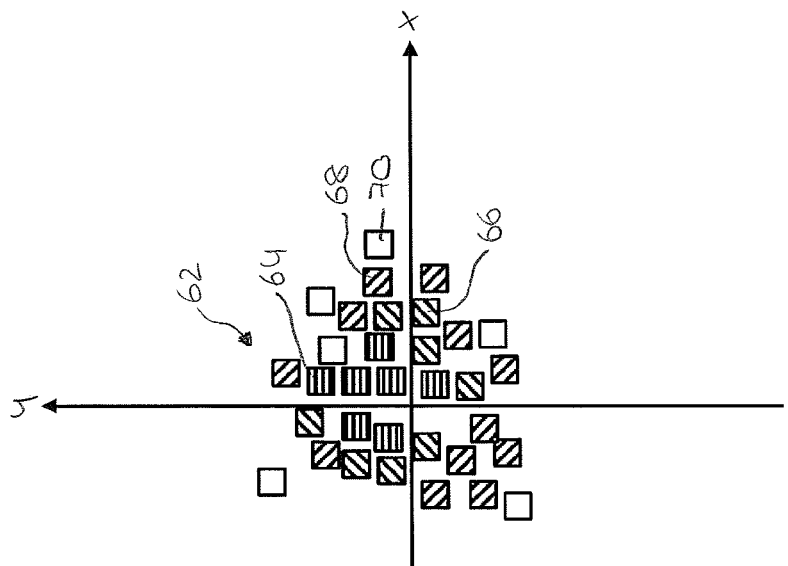
FIGS. 2A and 2B schematically show exemplary graphical illustrations visualizing a time-dependent x-y position of a pupil center of an eye, according to embodiments.

FIG. 1 shows an ophthalmic laser processing apparatus generally denoted 10. The apparatus 10 can be used to perform a laser treatment on an eye 12. The apparatus 10 comprises a laser device 14, a control device 16, an image capturing device 18 and a visualization device 20.

The laser device 14 comprises a laser source 22, which generates a laser beam 24 having pulse durations that are, for example, in the nanosecond range. The laser beam 24 has a suitable wavelength for the purpose of ablating (resecting) tissue of the eye 12. The wavelength of the laser beam 24 may, for example, lie in the infrared region (e.g., about 1 μm) or the wavelength may be shorter (right down to the UV region).

A beam expander 26, a scanning device 28 and a focusing device 30 are disposed downstream of the laser source 22 in a beam path of the laser beam 24. The order of succession of the beam expander 26, scanning device 28 and focusing device 30 along the direction of beam propagation may correspond to the order shown in FIG. 1. In other embodiments, at least a part of the scanning functionality of the scanning device 28, e.g., a longitudinal scanning functionality, may be incorporated in the beam expander 26 or the focusing device 30. In addition to this, one or more deflecting mirrors or other suitable beam guiding components may be disposed along the beam path.

The beam expander 26 is configured to enlarge the diameter of the laser beam 24 generated by the laser source 22. In the embodiment shown, the beam expander 26 includes a concave lens (having a negative refractive power) and a convex lens (having a positive refractive power) disposed in the beam propagation direction after the concave lens, as is typical for a Galilean telescope. In another embodiment, the beam expander 26 may include additional and/or different lenses (as e.g., two convex lenses of a Keplerian telescope).

The scanning device 28 is designed to control the position of a focus of the laser beam 24 (beam focus) in the transversal direction and in the output direction. In this case, the transversal direction describes the direction that is transverse in relation to the propagation direction of the laser beam 24 (denoted as x-y plane), and the output direction describes the propagation direction of the laser beam 24 after passing the focusing device 30 (denoted as the z-direction). For the purpose of transversally deflecting the laser beam 24, the scanning device 28 may comprise, for example, a pair of galvanometrically actuated deflection mirrors that can be tilted about mutually perpendicular axis. As an alternative or in addition to this, the scanning device 28 may have an electro-optical crystal or other components suitable for transversally deflecting the laser beam 24. The scanning device 28 may additionally comprise a lens that is longitudinally adjustable or that has a variable refractive power, or a deformable mirror, in order to influence the divergence of the laser beam 24 and, consequently, the longitudinal alignment of the beam focus. In the embodiment shown, the components for controlling the transversal alignment and longitudinal alignment of the beam focus are represented as an integral component. In another embodiment, the components may be disposed separately along the propagation direction of the laser beam 24.

The focusing device 30 is configured to focus the laser beam 24 onto the region of the eye 12 to be treated. The focusing device 30 may be, for example, an F-Theta objective.

The control device 16 comprises a control module 32 and an evaluating module 34. The control module 32 comprises a memory 36, in which at least one control program 38, having program instructions, and reference eye parameter values are stored. The program instructions, when executed by the control device 16, cause the beam focus to be moved in time and space in accordance with a predetermined eye processing pattern. The laser source 22 and the scanning device 28 are controlled by the control device 16 in a manner depending on the eye processing pattern and in a manner depending on any tracking data, the control module 32 receives from the evaluating module 34.

In the embodiment shown, the evaluating module 34 and the image capturing device 18 are comprised by an eye-tracker. In another embodiment, for example, the image capturing device 18 may be comprised by a different tracking device and/or the functionalities of the control module 32 and the evaluating module 34 may be included in a single module.

The image capturing device 18 is configured to acquire sectional images of the eye 12 containing at least the pupil 40 and the iris 42 of the eye 12. The image capturing device 18 may be, or comprise, a camera or any suitable measuring device for acquiring the sectional images. The evaluating module 34 receives image data from the image capturing device 18 that include the acquired sectional images, and is configured to compute tracking data from the image data tracking data. The tracking data include at least one of a position and an orientation of the eye 12 in three-dimensional space, a diameter of the pupil 40 of the eye 12 and a movement of the eye 12. The computed eye movement in this case comprises translational movements in the transversal direction and along the output direction as well as rotational movements at least around the optical axis of the eye 12 (denoted as φ-direction). In an alternative to this, the computed eye movement may comprise less, different or additional movement components.

The control device 16 is configured to cause, in dependence of the received tracking data, deviations of the beam focus position (in regard to the position predetermined in the eye processing pattern) in order to correct for the movement of the eye 12. The resulting deviations of the beam focus position are referred to as tracking corrections. The control device 16 is further configured to provide the tracking data to the visualization device 20. In the embodiment shown, the visualization device 20 comprises a monitor 44 and a printer 46 in order to visualize the tracking data. In another embodiment, one of the monitor 44 and the printer 46, and/or different devices may be comprised by the visualization device 20.

The visualization device 20 is configured to provide a visualization of a graphical illustration of the tracking data, as shown in FIGS. 2A to 4B. For the purpose of visualization, the control device 16 is configured to determine the tracking data on the basis of the image data in relation to each of a plurality of pulses of the laser beam 24. In an alternative to this, the control device 16 may be configured to determine the tracking data on the basis of the image data in relation to each of a plurality of pulse sequences (e.g., in relation to the first pulse of the pulse sequence or averaged over each of the pulses within the pulse sequence). The pulses may be, or may include, temporally successive pulses. It may be further provided that the control device 16 is configured to determine the tracking data on the basis of the image data in relation to each of a plurality of time points or time intervals different from the plurality of pulses of the laser beam 24.

Figure 2A:
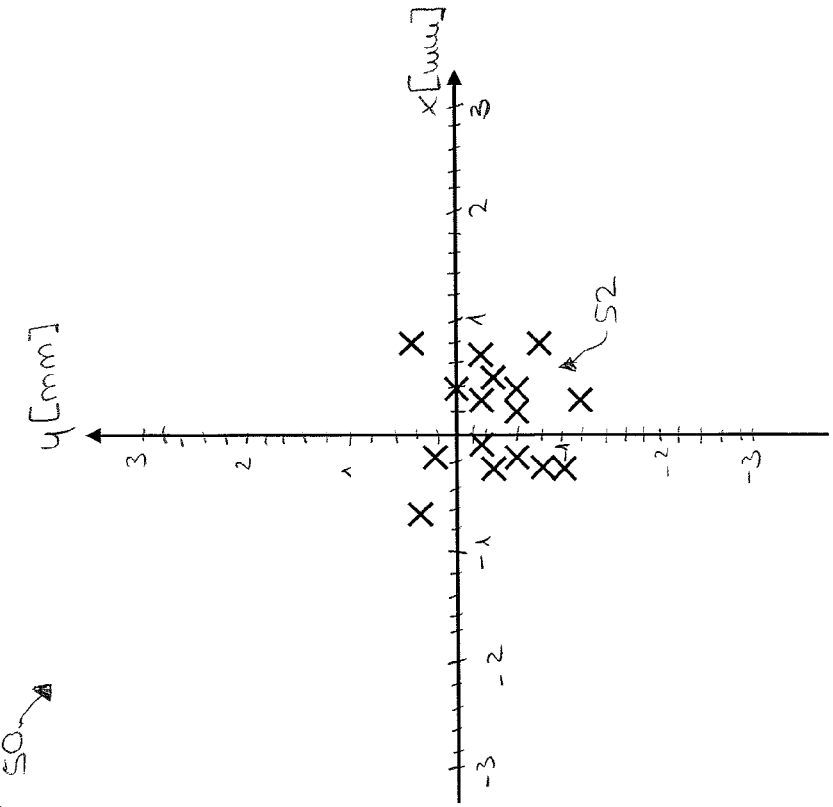

FIGS. 2A and 2B show schematic representations of graphical illustrations, denoted in general by 50 and 60, of positions of a pupil center of the eye 12. The positions are represented with respect to an x-y coordinate plane, which may be the transversal plane as defined with respect to FIG. 1. The x-y positions may be determined by the evaluating module 34 according to the embodiment shown in FIG. 1. The variations of the x-y positions may be, for example, caused by at least one of transversal head movements of the patient and movements of the eye 12 within its eye socket with respect to the apparatus 10.

In FIG. 2A, the graphical illustration 50 represents the positions of the pupil center as x-y offset values 52 with respect to an x-y reference position. In the visualization shown, the x-y reference position is defined by an x-value of 0 mm and a y-value of 0 mm. The graphical illustration 50 represents a point cloud of offset values 52 within the x-y coordinate plane which is spanned by two orthogonal axes in x- and in y-direction intersecting at the x-y reference position. In x- and in y-direction, offset values 52 are represented which lie within a range of −3 mm to +3 mm. Steps of 0.2 mm are considered. In an alternative to this, the graphical illustration 50 may represent smaller or larger ranges of offset values and/or smaller or larger steps. The range of offset values and/or the steps may not be the same in x- and y-direction. It may be further provided that the range of offset values and/or the steps size may be adjusted automatically based on the determined offset values. Each of the offset values 52 is represented by a cross in the x-y coordinate plane. In an alternative to this, the offset values 52 may be represented by different graphical objects such as, for example, dots, lines, circles, squares, triangles or asterisks. Furthermore, the offset values 52 may have different representations (as e.g., different colors or different graphical objects) for different pulses or pulse sequences of the laser beam 24.

Unlike FIG. 2A, in the graphical illustration 60 shown in FIG. 2B the x-y offset values 62 are not represented by graphical objects having identical appearance (as e.g., crosses). The appearance of the graphical objects depends on a frequency of the x-y offset values 62 determined on the basis of the image data acquired by the image capturing device 18 according to FIG. 1. In this case, the control device 16 may be configured to determine the frequency distribution.

In the visualization shown, the x-y offset values 62 are represented by squares which are filled with a frequency-dependent pattern. For example, x-y offset values occurring with a highest frequency are represented by squares 64 having lines in +x-direction, x-y offset values occurring with a second highest frequency are represented by squares 66 having lines in +x/+y-direction, x-y offset values occurring with a second smallest frequency are represented by squares 68 having lines in −x/+y-direction and x-y offset values occurring with a smallest frequency are represented by empty squares 70. In another visualization, the x-y offset values 62 may be represented through different graphical objects having frequency-dependent appearances. For example, different frequencies of the x-y offset values 62 may be represented through at least one of a different transparency and a different color of the graphical object. It may be further provided that a different number of frequency classes are represented.

In the visualization shown, the axes in x- and y-direction do not provide a scaling. In another visualization, the x-y coordinate plane in the graphical illustration 60 may be spanned by axes in x- and in y-direction according to FIG. 2A. In addition or alternatively, a legend of the frequencies may be included in the graphical illustration 60.

In the graphical illustrations 50, 60 shown in FIGS. 2A and 2B, a distance of the point cloud of offset values 52, 62 with respect to the x-y-reference position give an indication for an alignment of the patient's eye 12 with respect to the apparatus 10 according to FIG. 1 during the course of laser processing. Furthermore, the spatial extension of the point cloud of offset values 52, 62 provides additional information regarding the course of laser processing, as, for example, on the nervousness of the patient.

It is to be understood that in a visualization different from the visualization shown in FIGS. 2A and 2B, the graphical illustrations 50, 60 may represent values of a different eye parameter (as e.g., a position of the eye in z-direction or in φ-direction).

In FIGS. 3A and 3B, schematic representations of visualized graphical illustrations, denoted in general by 80 and 90, of a frequency of z- and φ-positions of the eye 12 are shown, respectively. The frequency distribution is represented in the form of a histogram 82, 92 including bars having frequency-dependent size.

FIG. 3A shows the frequency of the eye position with respect to a z-direction oriented in the output direction (as defined with respect to FIG. 1). The illustrated variations in z-positions of the eye may correspond to movements of the patient's head with respect to the apparatus 10 during the course of the laser processing. The z-positions may be determined by the control device 16 according to FIG. 1. In the visualization shown, the graphical illustration 80 represents offset values with respect to a reference z-position with a z-value of 0 mm. Offset values are represented which lie within a range of −2 mm to +2 mm. Steps of 0.2 mm are considered.

In FIG. 3B, the frequency of the eye position with respect to a φ-direction (as defined with respect to FIG. 1) is shown. The illustrated variations of φ-positions of the eye may be indicative of an amount of rotation of the eye 12 around its optical axis (cyclorotation). The cyclorotation may occur during the course of laser processing, for example, in accordance with a variation of the diameter of the pupil 40 due to varying light conditions. The φ-positions may be determined by the control device 16 according to FIG. 1. In the visualization shown, the graphical illustration 90 represents offset values with respect to a reference φ-position with a φ-value of 0°. Offset values are represented which lie within a range of −3° to +3°. Steps of 0.2° are considered.

In a visualization different from the visualizations shown in FIGS. 3A and 3B, the graphical illustrations 80, 90 may represent smaller or larger ranges of values and/or smaller or larger steps. It may be further provided that the range of values and/or the steps size may be adjusted automatically based on the determined offset values. In addition or alternatively, a legend of the frequencies may be included in the graphical illustrations 80, 90. The legend may be, for example, in the form of different colored bars, numerical values (e.g., representing absolute values or frequencies) assigned to the bars or assigned to an axis extending in parallel to the bars. It is to be understood that the graphical illustrations 80, 90 may represent frequencies of a different eye parameter (as e.g., a position of the eye in x- or in y-direction or a rotation around a different axis).

In the visualizations shown in FIGS. 2A to 3B, the reference positions are defined by a value of 0. In other visualizations, the positions may be represented with respect to a different reference position (e.g., defined by global coordinates). It may be provided that the reference position is determined before the laser processing starts. In an alternative to this, the reference position may be the position determined in relation to the first of the plurality of pulses of the laser beam 24.

FIGS. 4A and 4B show schematic representations of a visualization of a graphical illustration, denoted in general by 100 and 110, of a range of values of a diameter of the pupil 40 of the eye 12. The control device 16 according to FIG. 1 may be configured to determine the pupil diameters on the basis of the image data received from the image capturing device 18. The eye 12 may perform cyclorotations in accordance with the change of the pupil diameter. The control device 16 in this case may be further configured to determine the eye position with respect to the φ-direction (cf. FIG. 3B) and/or the position of the pupil center with respect to the x-y coordinate plane (cf. FIGS. 2A and 2B) corresponding to the determined pupil diameters.

In the visualization shown in FIGS. 4A and 4B, the graphical illustrations 100, 120 represent the pupil diameters in an x-y coordinate plane, which may be the transversal plane as defined with respect to FIG. 1. The graphical illustrations 100, 120 in this case show a graphical object for a specific value of the pupil diameter at the respective x-y position of the pupil center of the eye 12. In another visualization, the values of the pupil diameters may be shown in a different (two-dimensional) visualization area. Further, the directions along the x-axis and along the y-axis may be denoted, for example, as nasal to temporal and superior to inferior, respectively. It may be provided that the values of the pupil diameters are represented without any reference to a visualization area.

In FIG. 4A, the graphical illustration represents a reference range of values of the pupil diameter as a solid rectilinear line 102 in the x-y coordinate plane. The extension of the solid rectilinear line 102 is limited by a lower limit reference value and an upper limit reference value. In the visualization shown, the lower and the upper limit reference values are represented in the graphical illustration 100 through circles 104, 106 filled with lines in x-direction. The circle 104 representing the lower limit reference value has a smaller diameter than the circle 106 representing the upper limit reference value. In a different visualization, the lower and the upper limit reference values may be represented through a different graphical object or may not be represented in the graphical illustration 100. The control device 16 according to FIG. 1 may be configured to determine and to store (e.g., in the memory 36 of the control module 32) the reference values of pupil diameters. The reference values may be determined in the course of a reference measurement of the pupil diameters of the patient previously to the laser processing. In the visualization shown, the lower limit reference value is indicative of a pupil diameter determined in accordance with a first brightness and the upper limit reference value is indicative of a pupil diameter determined in accordance with a second (smaller than the first) brightness. The first and the second brightness may limit a larger range of pupil diameter values as typically occurring during the course of laser processing the eye 12.

In the graphical illustration 100 in FIG. 4A, the range of determined pupil diameter values during the course of laser processing is represented by a box 108. The extension of the box 108 is limited by a bar 110 representing a lower limit pupil diameter and a bar 112 representing an upper limit pupil diameter. The bars 110, 112 are oriented orthogonally to the solid rectilinear line 102 representing the reference range of pupil diameter values. In the visualization shown, the box 108 is superimposed over the solid rectilinear line 102. In a different visualization, the box 108 may be represented, for example, in parallel to the solid rectilinear line 102. The range of determined pupil diameter values may be represented in the graphical illustration 100 by a different graphical object (e.g., by crosses on or parallel to the solid rectilinear line 102). It may be further provided that the box 108 represents pupil diameter values within, for example, a standard deviation of the determined pupil diameters.

In the graphical illustration 100 in FIG. 4A, an average value of the determined pupil diameter values is represented by a bar 114 superimposing the box 108. The bar 114 is extending transversely to the rectilinear line 102. In the visualization shown, a proportion of distances of the bar 114 for the average value from the bars 110, 106 for the upper and lower limit pupil diameter values corresponds to a proportion of differences between the average value and the upper and lower limit pupil diameter values. In another visualization, the proportions do not correspond. It may be provided that the graphical object for the average value may be different from the bar 114 (e.g., a cross or an asterisk). Alternatively or in addition, it may be provided that different values (as e.g., a median value of the determined pupil diameter values and/or upper and lower limits of a standard deviation of the determined pupil diameter values) are represented by graphical objects in the graphical illustration 100.

The control device 16 according to FIG. 1 may be configured to determine at least one of the upper and lower limit reference values and the average value based on the determined pupil diameter values. In the visualization shown, numerical values of the pupil diameters and the respective amount of cyclorotation are shown in the graphical illustration 100 in accordance with the circles 104, 106 representing the upper and lower limit reference values. In another visualization, further numerical values may be shown (e.g., for the average value) or no numerical values may be shown.

In addition to the graphical illustration 100 according to FIG. 4A, in the graphical illustration in FIG. 4B, a second reference range of pupil diameter values is represented by a dashed rectilinear line 122. The dashed rectilinear line 122 represents in this case a reference range of pupil diameters based on averaged empirical data (e.g., by different patients). In the visualization shown, die dashed rectilinear line 122 is limited by a lower limit empirical value and an upper limit empirical value. In the visualization shown, the lower and the upper limit empirical values are represented in the graphical illustration 110 through circles 124, 126. The circle 124 representing the lower limit empirical value has a smaller diameter than the circle 126 representing the upper limit empirical value. In a different visualization, the lower and the upper limit empirical values may be represented through a different graphical object or may not be represented in the graphical illustration 110. The control device 16 according to FIG. 1 may be configured to determine and to store (e.g. in the memory 36 of the control module 32) the averaged empirical data of pupil diameter values.

In the visualization shown, the dashed rectilinear line 122 is superimposed by the solid rectilinear line 120 and the box 108. In a different visualization, the dashed rectilinear line 122 may be represented, for example, in parallel to the solid rectilinear line 102 and/or to the box 108. The range of averaged empirical data of pupil diameter values may be represented in the graphical illustration 110 by a different graphical object (e.g. by crosses in parallel to the solid rectilinear line 102). It may be further provided that the range of averaged empirical data of pupil diameter values is the only reference range represented in the graphical illustration 110.

In an advantageous embodiment of the apparatus according to FIG. 1, the control device 16 is configured to cause a visualization of at least one of the graphical illustrations 50, 60, 80, 90, 100, 110 according to FIGS. 2A to 4B during a phase of beam emission and update at least one of the graphical illustrations 50, 60, 80, 90, 100, 110 as the phase of beam emission proceeds. The graphical illustration 50, 60, 80, 90, 100 or/and 110 in this case allows and facilitates a follow-up control of the laser processing and a decision on whether to proceed or stop the treatment of the eye.

The phase of beam emission advantageously corresponds to the whole duration of laser processing the eye 12. As an alternative to this, the phase of beam emission may correspond to, for example, at least half of the duration of laser processing. The graphical illustration 50, 60, 80, 90, 100 or/and 110 in this case provides quality assurance of the course of laser processing.

The invention claimed is:

1. An ophthalmic laser processing apparatus comprising:
a laser device configured to output a pulsed laser beam towards an eye, the laser beam having a beam focus;
a camera positioned to capture an image of the eye and configured to provide image data;
a control device configured to detect eye movement based on the image data and to control the beam focus temporally and spatially based on a predetermined eye processing pattern and the detected eye movement, the control device comprising a computer processor and a memory that stores program instructions that can be executed by the computer processor; and
a visualization device controlled by the control device to output a graphical illustration for an eye parameter describing a position of the eye, the visualization device comprising a computer monitor, the graphical illustration representing a frequency distribution of a value of the eye parameter determined on the basis of the image data in relation to each of a plurality of different time points or time intervals;
the control device further configured to:
determine the value of the eye parameter in relation to each of a plurality of pulses of the pulsed laser beam;
determine the frequency distribution of the value of the eye parameter on the basis of the determined parameter values, the frequency distribution determined in relation to each of the plurality of different time points or time intervals;
cause the visualization device to output the graphical illustration representing the frequency distribution of the value of the eye parameter during a phase of beam emission; and
update the graphical illustration as the phase of beam emission proceeds.

2. The apparatus of claim 1, wherein the eye parameter is a position of a pupil center.

3. The apparatus of claim 2, wherein the position of the pupil center is a position with respect to an x-y coordinate plane oriented orthogonally to an output direction of the laser beam.

4. The apparatus of claim 1, wherein the eye parameter is an eye position with respect to a z-axis oriented in an output direction of the laser beam.

5. The apparatus of claim 1, wherein the eye parameter is indicative of a rotational position of the eye.

6. The apparatus of claim 5, wherein the eye parameter indicates an amount of cyclorotation of the eye.

7. The apparatus of claim 3, wherein the graphical illustration represents the position of the pupil center as an x-y offset with respect to an x-y reference position of the pupil center, wherein the x-y reference position is defined as an x-value of 0 and a y-value of 0 in the x-y coordinate plane.

8. The apparatus of claim 1, wherein the graphical illustration represents the value of the eye parameter by a graphical object having identical appearance for each time point or time interval.

9. The apparatus of claim 1, wherein the graphical illustration represents the value of the eye parameter in relation to each of a plurality of pulses of the pulsed laser beam.

10. The apparatus of claim 1, wherein the graphical illustration represents different frequencies of the value of the eye parameter through at least one of different degrees of transparency and different colors of a graphical object.

11. The apparatus of claim 1, wherein the graphical illustration represents the frequency distribution in the form of a histogram including bars having a frequency-dependent size.

12. The apparatus of claim 1, wherein the control device is configured to:
determine a pupil diameter value of a pupil diameter on the basis of the image data in relation to each of a plurality of pulses of the laser beam; and
determine upper and lower limit values for the range of values based on the determined pupil diameter values, wherein the graphical illustration represents the determined upper and lower limit values.

13. The apparatus of claim 12, wherein:
the control device is configured to determine an average value or a median value of the pupil diameter based on the determined pupil diameter values; and
the graphical illustration further represents the determined average or median value.

14. The apparatus of claim 13, wherein:
the graphical illustration represents the upper and lower limit values and the determined average or median value by respective graphical objects;
a graphical object for the average or median value is located between graphical objects for the upper and lower limit values; and
a proportion of distances of the graphical object for the average or median value from the graphical objects for the upper and lower limit values corresponds to a proportion of differences between the average or median value and the upper and lower limit values.

15. The apparatus of claim 1, wherein:
the graphical illustration further represents at least one reference range of values of a pupil diameter; and
a lower limit value of the reference range of values is indicative of a value of the pupil diameter at a first reference brightness and an upper limit value of the reference range of values is indicative of a value of the pupil diameter at a second reference brightness.

16. The apparatus of claim 1, wherein the graphical illustration represents the range of values and the reference range of values in a two-dimensional visualization area spanned by an x-y coordinate plane oriented orthogonally to an output direction of the laser beam.

17. The apparatus of claim 16, wherein the graphical illustration includes at least one graphical object representing a value of a pupil diameter and having an x-y position in the visualization area corresponding to an x-y position of the pupil center in the x-y coordinate plane at the value of the pupil diameter.

18. The apparatus of claim 15, wherein the graphical illustration includes a rectilinear line to visualize the reference range of values and one or more bars extending transversely to the rectilinear line to visualize the range of values.

19. The apparatus of claim 18, wherein the bars are part of a box superimposed over the rectilinear line.

* * * * *